(12) United States Patent
Surti

(10) Patent No.: US 8,945,153 B2
(45) Date of Patent: Feb. 3, 2015

(54) ENDOSCOPIC APPARATUS HAVING A CLIP DEVICE

(75) Inventor: Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 2121 days.

(21) Appl. No.: 11/758,369

(22) Filed: Jun. 5, 2007

(65) Prior Publication Data

US 2007/0282353 A1 Dec. 6, 2007

Related U.S. Application Data

(60) Provisional application No. 60/811,028, filed on Jun. 5, 2006.

(51) Int. Cl.
| | | |
|---|---|---|
| A61B 17/10 | (2006.01) | |
| A61B 19/02 | (2006.01) | |
| A61B 17/122 | (2006.01) | |
| A61B 17/128 | (2006.01) | |
| A61B 17/00 | (2006.01) | |

(52) U.S. Cl.
CPC .......... *A61B 19/0248* (2013.01); *A61B 17/122* (2013.01); *A61B 17/1285* (2013.01); *A61B 2017/003* (2013.01); *A61B 2019/025* (2013.01)
USPC ...................................................... 606/142

(58) Field of Classification Search
USPC .................. 606/139, 142, 220, 151, 157, 158
See application file for complete search history.

(56) References Cited

U.S. PATENT DOCUMENTS

| | | | | |
|---|---|---|---|---|
| 5,304,183 A | * | 4/1994 | Gourlay et al. | 606/142 |
| 5,445,167 A | * | 8/1995 | Yoon et al. | 128/898 |
| 5,569,274 A | * | 10/1996 | Rapacki et al. | 606/158 |
| 5,868,663 A | * | 2/1999 | Katsurada et al. | 600/107 |
| 6,814,742 B2 | * | 11/2004 | Kimura et al. | 606/151 |
| 6,827,683 B2 | | 12/2004 | Otawara | |
| 7,776,066 B2 | * | 8/2010 | Onuki et al. | 606/220 |
| 2002/0177861 A1 | * | 11/2002 | Sugiyama et al. | 606/151 |
| 2003/0069592 A1 | * | 4/2003 | Adams et al. | 606/142 |
| 2003/0078598 A1 | * | 4/2003 | Ginn et al. | 606/142 |
| 2004/0092978 A1 | | 5/2004 | Surti | |
| 2005/0143767 A1 | * | 6/2005 | Kimura et al. | 606/158 |
| 2005/0261711 A1 | * | 11/2005 | Okada et al. | 606/153 |
| 2006/0259043 A1 | * | 11/2006 | Miyamoto et al. | 606/139 |

* cited by examiner

*Primary Examiner* — Melanie Tyson
*Assistant Examiner* — Alexander Orkin
(74) *Attorney, Agent, or Firm* — Brinks Gilson & Lione

(57) ABSTRACT

A hemostatic clip delivery system cooperable with an elevator of an endoscope and a method of treating a target with the system are disclosed. The system comprises a delivery apparatus comprising an operating wire, an outer sheath and a handle. The operating wire is cooperable with the elevator of the endoscope and slidably disposed within the outer sheath. The system further comprises a hemostatic clip cooperable with the delivery apparatus. The clip comprises a first retainer, a plurality of arms extending distally from the first retainer, and a sliding ring disposed about the plurality of arms. The arms are shaped so that the arms tend to be spaced apart from each other. The sliding ring is configured to close the arms together as the elevator engages and moves the sliding ring toward the arms by retraction of the operating wire.

20 Claims, 6 Drawing Sheets

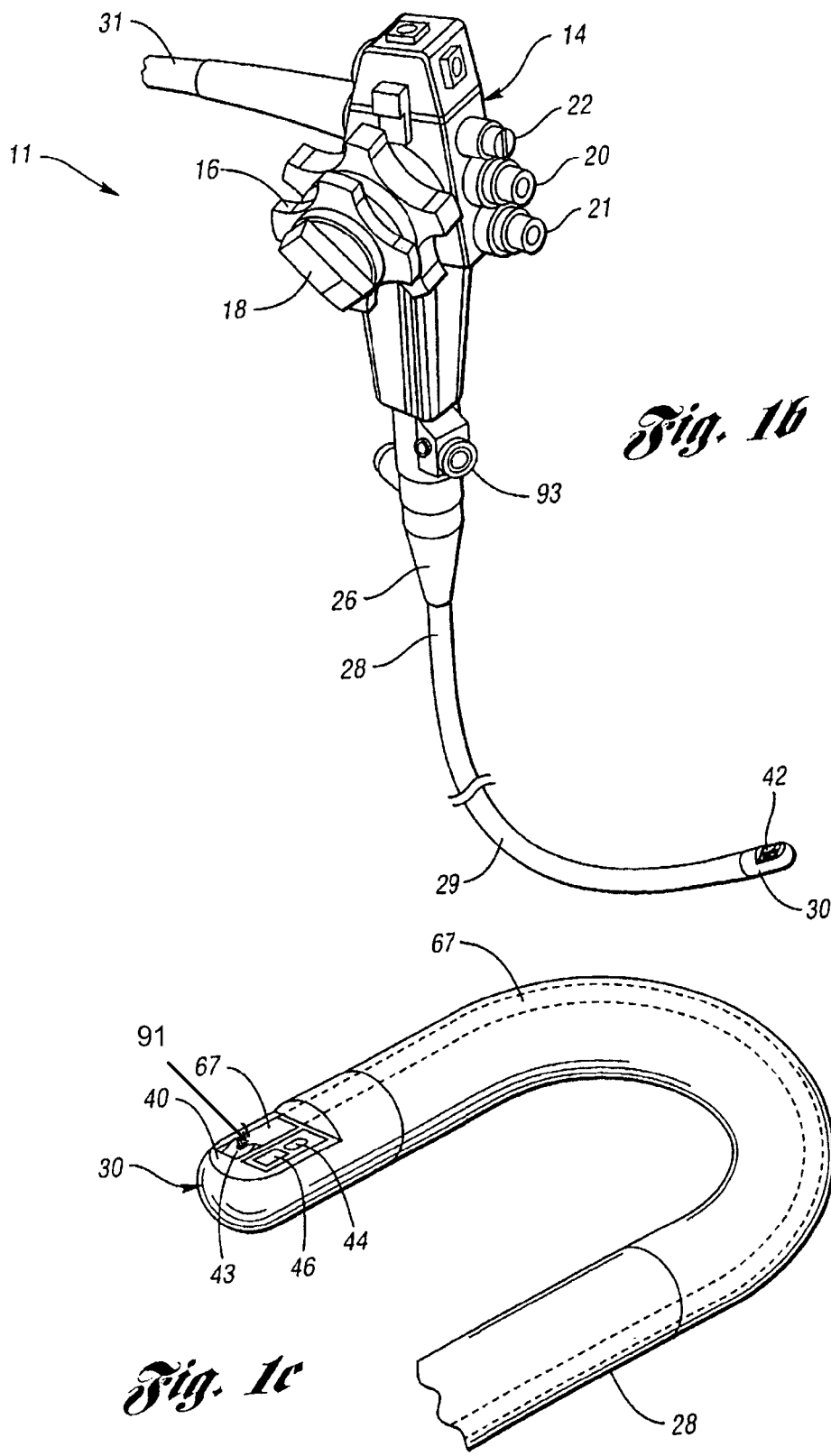

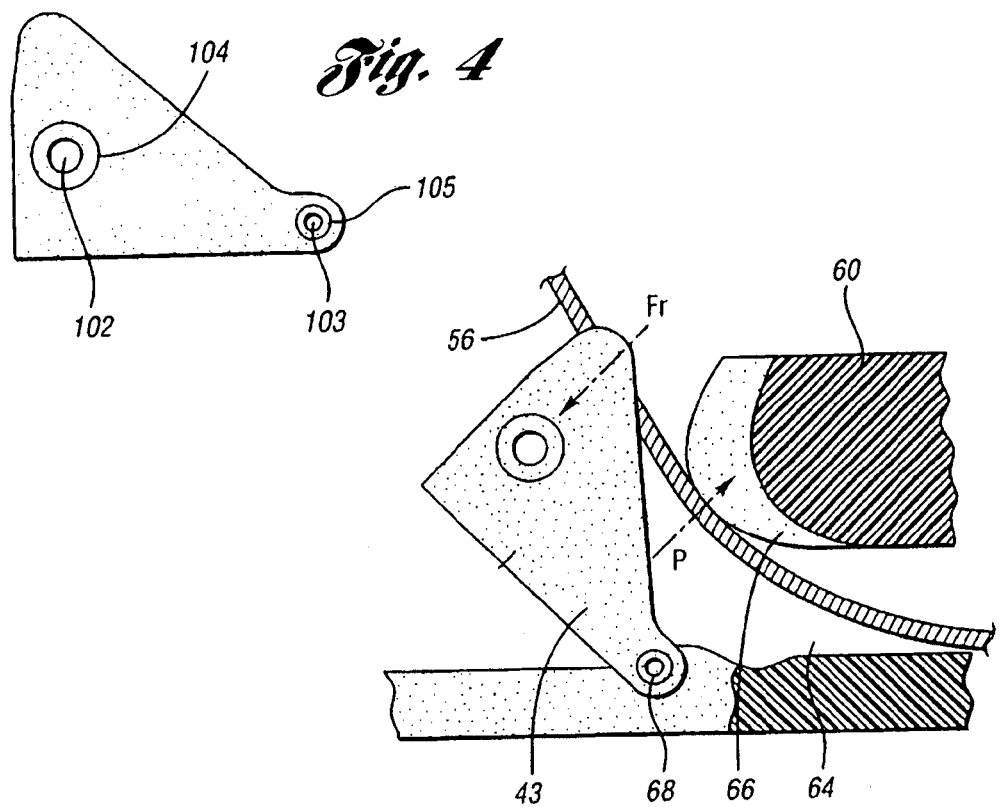

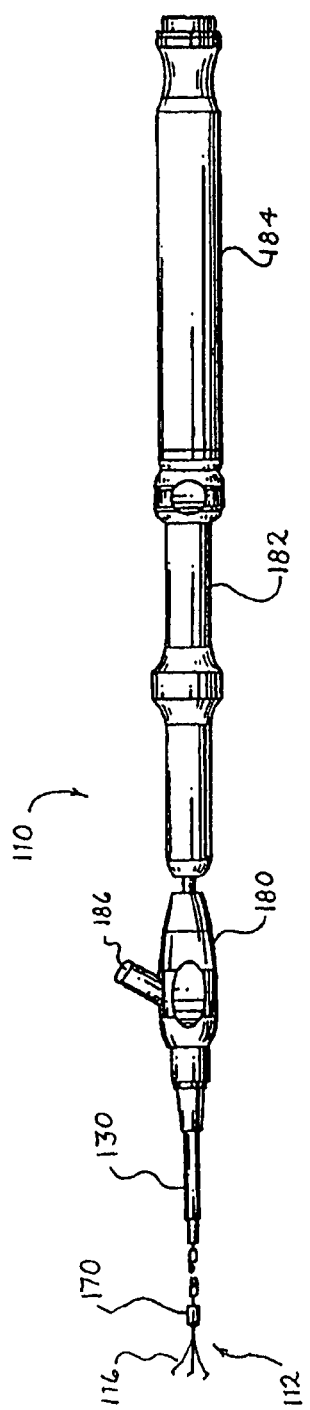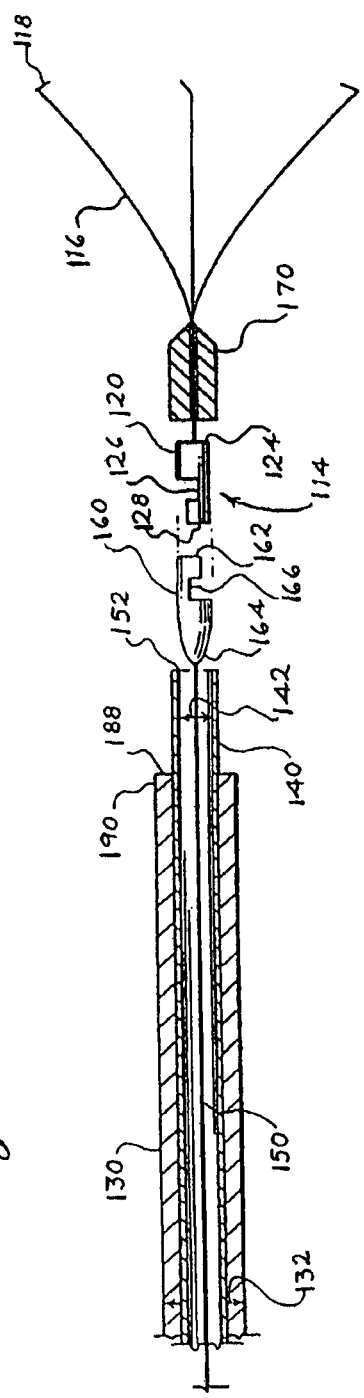

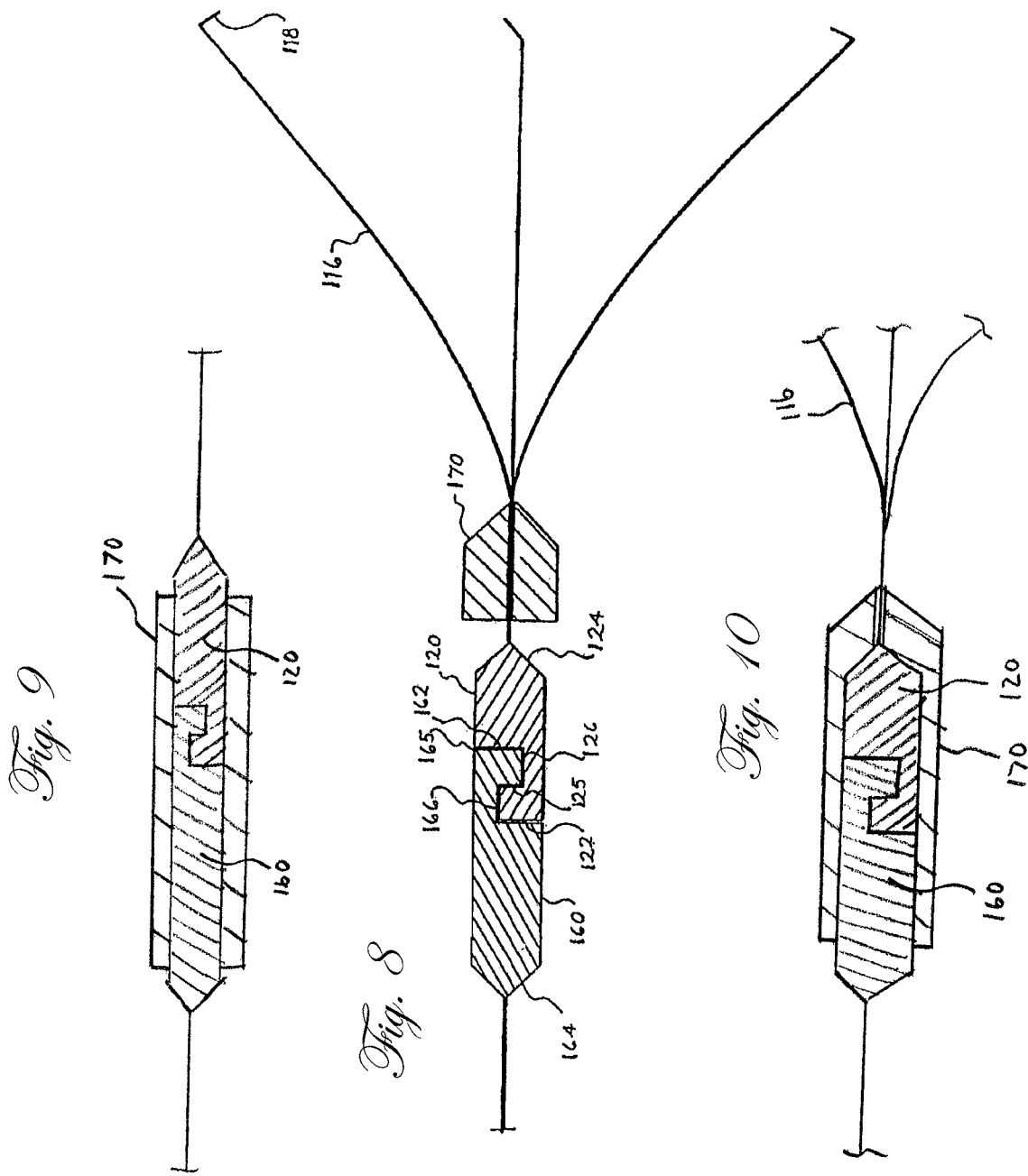

ENDOSCOPIC APPARATUS HAVING A CLIP DEVICE

CROSS-REFERENCE TO RELATED APPLICATIONS

This application claims the benefit of U.S. Provisional Application Ser. No. 60/811,028, filed on Jun. 5, 2006, entitled "ENDOSCOPIC APPARATUS HAVING A CLIP DEVICE," the entire contents of which are incorporated herein by reference.

FIELD OF THE INVENTION

The present invention relates to medical devices, and more particularly, to endoscopes having a medical instrument elevator.

BACKGROUND OF THE INVENTION

Endoscopic devices have been commonly used for various procedures, typically in the abdominal area. Endoscopy is the examination and inspection of the interior of body organs, joints or cavities through an endoscope. Endoscopy allows physicians to peer through the body's passageways. An endoscopic procedure may be used to diagnose various conditions by close examination of internal organ and body structures and may also guide therapy and repair, such as the removal of torn cartilage from the bearing surfaces of a joint. A biopsy, a procedure involving tissue sampling for pathologic testing, may also be performed under endoscopic guidance. For example, endoscopic procedures include the following known procedures: gastroscopy, sigmoidoscopy and colonoscopy, esophago gastro duodenoscopy (EGD), endoscopic retrograde cholangiopancreatography (ERCP), and bronchoscopy.

The use of endoscopic treatments has recently increased for some diseases occurring in the gastrointestinal or pancreatobiliary duct systems. Endoscope systems are used frequently for diagnostic procedures, including contrast imaging of biliary or pancreatic ducts. Endoscopes are also used in procedures for retrieving gallstones that exist in the common bile duct and elsewhere.

Typically, these treatments are performed in the pancreatic duct, bile duct, and the hepatic duct by positioning the distal end of an endoscope in the vicinity of the duodenal papilla. Once the endoscope is in place, a wire guide is delivered to the target anatomy via the working channel of the endoscope. In order to guide the wire guide (or other medical instruments), out of the working channel of the endoscope, a rigid elevator is typically used to orient or deflect the distal end of the wire guide. When the distal end of the wire guide is properly oriented, the wire guide is inserted into the target anatomy.

At this point in the procedure, a catheter or similar treatment instrument can be passed over the wire guide either in a conventional over-the-wire style or in a rapid exchange style to the target anatomy. In order to limit movement of the wire guide relative to the target anatomy, the distal or proximal ends of the guide wire can be locked relative to the endoscope.

Many current endoscopic systems include endoscopes having an elevator used to orient and/or to lock the distal end of the catheter or wire guide. In many of such endoscopes, the elevator includes a v-shaped groove. The v-shaped groove is typically used to guide the catheter or wire guide to a central position relative to the endoscope. The elevator having a v-shaped groove is further used to lock the distal end of the catheter or guide wire.

Manufacturers have been challenged in providing devices that are used in cooperation with current endoscopic systems. There is a need to provide devices that may be used in cooperation with current endoscopic systems.

BRIEF SUMMARY OF THE INVENTION

The present invention generally provides an endoscopic apparatus having a clip device that cooperates with the endoscopic apparatus.

In one embodiment, the present invention provides a hemostatic clip delivery system cooperable with an endoscope having an elevator with a slot formed thereon. The system comprises a delivery apparatus and a hemostatic clip cooperable with the delivery apparatus. The delivery apparatus comprises an operating wire, an outer sheath, and a handle. The operating wire is cooperable with the elevator of the distal tip of the endoscope and is slidably disposed within the outer sheath. The clip comprises a first retainer, a plurality of arms extending distally from the first retainer, and a sliding ring disposed about the plurality of arms. The arms are formed of a resilient material and are shaped so that the arms tend to be spaced apart from each other. The sliding ring is configured to close the arms together as the elevator engages and moves the sliding ring toward the arms by retraction of the operating wire.

In another embodiment, the present invention provides an endoscope having the hemostatic clip device for hemostasis. The endoscope comprises an insertion tube extending to a distal tip having an elevator. The delivery apparatus is configured to be disposed through the insertion tube and is cooperable with the elevator. The hemostatic clip is cooperable with the delivery apparatus. The endoscope further comprises a control system in communication with the insertion tube and the elevator for movement of the insertion tube and elevator during operation of the endoscope.

In another example, the present invention provides a method of treating a target in a patient. The method comprises providing the hemostatic clip delivery system cooperable with an endoscope having an elevator with a slot formed thereon. The method further comprise introducing the outer sheath through the endoscope to the target and retracting the outer sheath to expose the sliding ring and the clip to extend the arms to an open position. The method further comprises slidably disposing the operating wire within the slot of the elevator and retracting the operating wire to engage the elevator with the sliding ring. Furthermore, the method comprises moving the elevator outwardly so that the sliding ring slides over the arms causing the arms to close on the target.

Further objects, features, and advantages of the present invention will become apparent from consideration of the following description and the appended claims when taken in connection with the accompanying drawings.

BRIEF DESCRIPTION OF THE DRAWINGS

FIG. 1b is a perspective view of the endoscope depicted in FIG. 1a;

FIG. 1c is an elevated view of a distal tip of the endoscope in accordance with one embodiment of the present invention;

FIG. 4 is a side view of an elevator in accordance with one embodiment of the present invention;

FIG. 5 is a cross-sectional view of the tip of the endoscope of FIG. 1, depicting a wire guide secured by an elevator;

FIG. 6 is an illustration of one embodiment of the clip device of the present invention;

FIG. 7 is an illustration of a portion of the clip device of the present invention before the retainers are joined;

FIG. 8 is an illustration of a portion of the clip device of the present invention after the retainers are joined;

FIG. 9 is an illustration of a portion of the clip device of the present invention showing a sliding ring enclosing the retainers prior to delivery; and FIG. 10 is an illustration of a portion of the clip device of the present invention showing a sliding ring having first and second cross-sections.

DETAILED DESCRIPTION OF THE INVENTION

The present invention provides a hemostatic clip delivery system cooperable with an elevator of an endoscope. The system is used for endoscopic marking, and hemostasis mucosal/submucosal defects in the upper gastrointestinal tract, bleeding ulcers, arteries, and polyps in the gastrointestinal tract. Embodiments of the present invention provide a clip device and a delivery apparatus for the clip device that is cooperable with an endoscope having an elevator at its distal tip. The elevator of the endoscope is used to deploy the clip device for hemostasis.

Figure 1A:
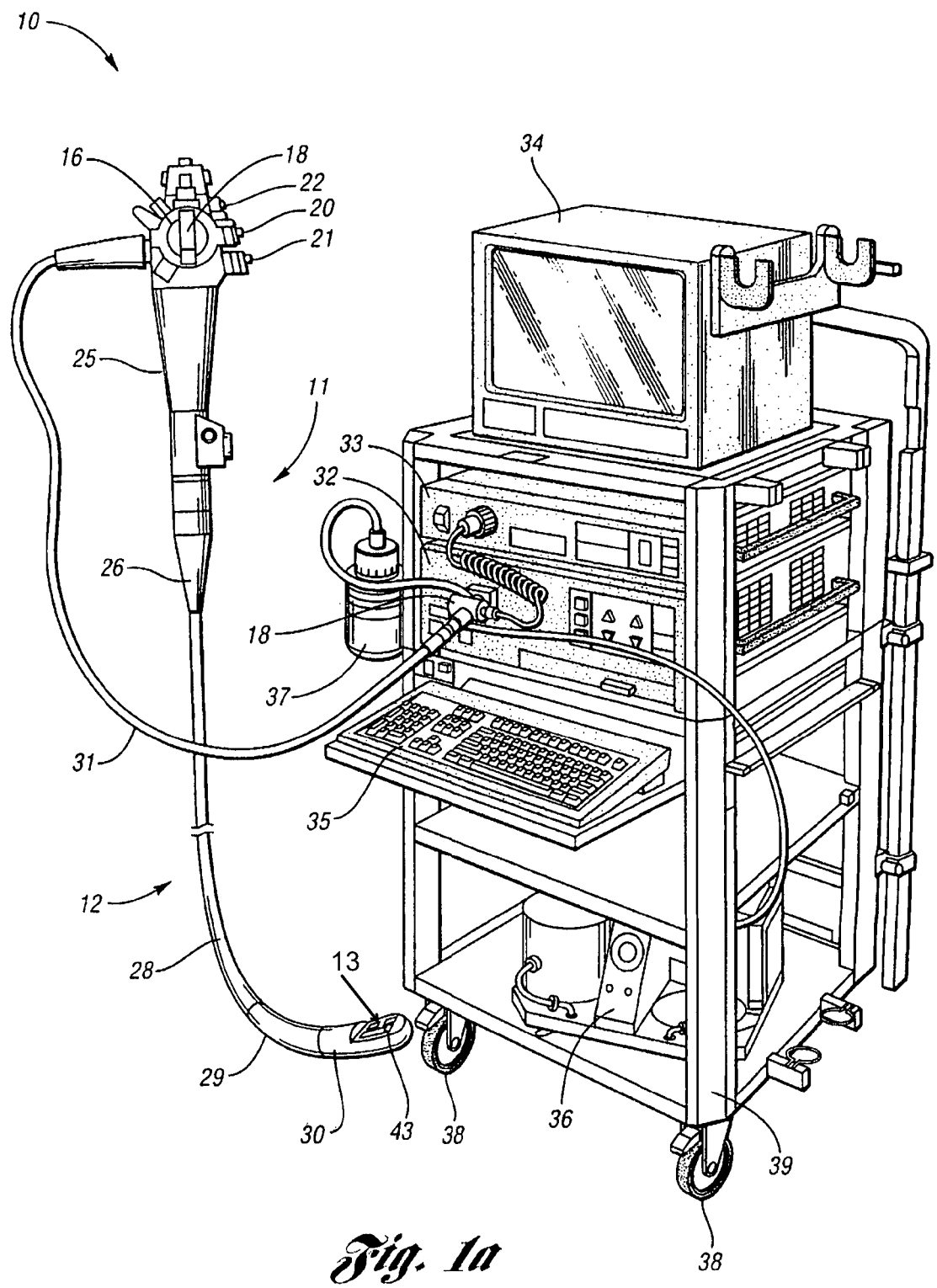
FIG. 1a is a perspective view of an endoscopic system comprising an endoscope in accordance with one embodiment of the present invention.
Figure 2:
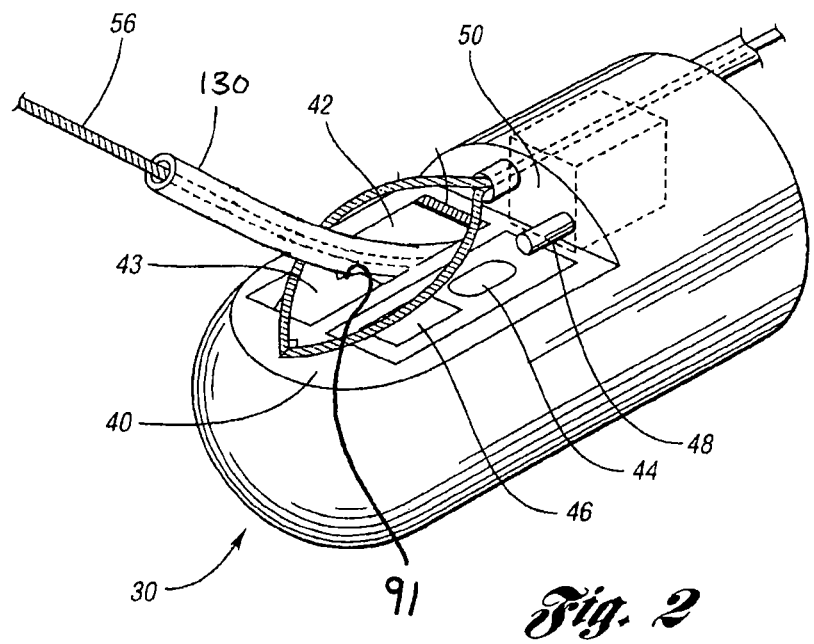
FIG. 2 is an enlarged view of the distal tip of the endoscope in accordance with one embodiment of the present invention.
Figure 3:
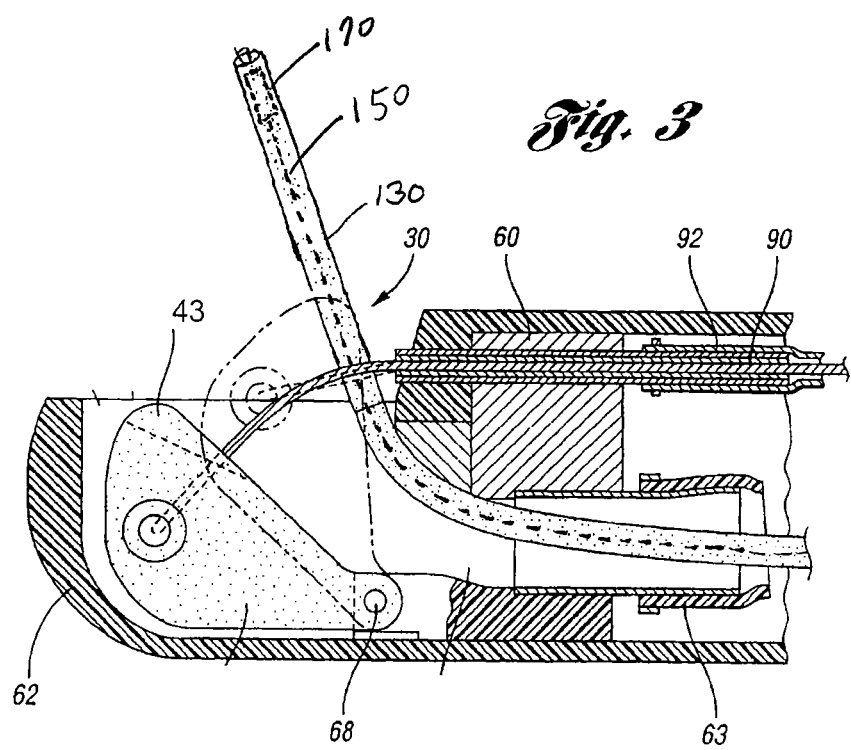
FIG. 3 is a cross-sectional view of the distal tip of the endoscope insertion portion of the endoscope taken along line 3-3.

FIGS. 1-3 illustrate an endoscopic system comprising an endoscope having an elevator with a distal tip. Additional details relating to the endoscopic system are described in U.S. Pat. No. 6,827,683, entitled "ENDOSCOPE SYSTEM AND MEDICAL TREATMENT METHOD" issued Dec. 7, 2004 to Takashi Otawara, which is incorporated herein by reference in its entirety.

FIG. 1a illustrates an endoscopic system 10 comprising an endoscope 11 in accordance with one embodiment of the present invention. In this embodiment, the endoscope 11 comprises an insertion tube 12 to be inserted into a body cavity for various endoscopic procedures including gastroscopy, sigmoidoscopy and colonoscopy, esophago gastro duodenoscopy (EGD), endoscopic retrograde cholangiopancreatography (ERCP), and bronchoscopy. As shown, the endoscope 11 comprises an insertion tube 12 having a plurality of channel ports 13 through which endoscopic units may be disposed. In one embodiment, endoscopic units disposed in one of the ports may include one embodiment of an improved elevator having a tip.

As shown in FIGS. 1a and 1b, the endoscope 11 further include a control system 14 that is in mechanical and fluid communication with the insertion tube 12. The control system 14 is configured to control the insertion tube 12 and endoscopic parts disposed therein. As shown, the control system 14 includes first and second control knobs 16, 18. The control knobs 16, 18 are configured to be in mechanical communication with the insertion tube 12. The control knobs 16, 18 allow the physician to control and guide, by known means, the insertion tube 12 through vessels and cavities of a patient. The control system 14 further includes valve switches (e.g., suction valve 20, air/water valve 21, camera valve 22), each of which are in communication to one of the channel ports 13 of the insertion tube 12. For example, the suction valve switch 20, when activated, allows a vacuum from a suction source through a suction channel port for suctioning unwanted plaque and debris from the patient. In one example, the distal end of the insertion tube 12 is inserted, rectally or orally, to a predetermined endoscopic location within a patient. Insertion of the insertion tube 12 may be rectally or orally depending on the endoscopic procedure.

In this embodiment, the insertion tube 12 comprises an operating portion 25 connected to the control system 14 and extending to an insertion portion protecting member 26. A control system 20 is connected to the operating portion 25 and is configured to control the insertion tube 12. In this embodiment, the insertion tube 12 is composed of components that include a flexible tube 28, a flexure 29 connected to the flexible tube 28, and an endoscope tip 30 connect to the flexure 29. A universal cord 31, on one end, is connected and in communication with the control system 20. On the other end, the cord 31 has a connector 18 attached thereto. The connector 18 is in communication to a light guide tube and electrical contact, and is connected to a light source apparatus 32 and an image processing apparatus 33 (external devices). These external devices may include a monitor 34, an input keyboard 35, a suction pump apparatus 36, and an irrigation bottle 37, and other suitable apparatus are installed on a rack 39 equipped with rollers 38.

As shown in FIGS. 1c and 2, a cutout 40 is formed on the outer circumferential surface of the tip 30. In this embodiment, a channel opening 42 is formed on one side of the cutout 40, and an objective lens 44 and a light source 46 are disposed on another side of the cutout 40 for imaging. Both the objective lens 44 and the light source 46 are positioned adjacent to the channel opening 42. The tip 30 further comprises a nozzle 48 extending from a back wall surface 50 of the cutout 40. The nozzle 48 allows a stream of water, air, or the like to be sprayed towards the outer surface of the objective lens 44 to clean the lens surface.

FIGS. 1c and 2 further illustrate the elevator 43 comprising a grasping slot 91 in accordance with one embodiment of the present invention. The grasping slot may take on any suitable shape or form for grasping of a medical device. In this embodiment, the grasping slot 91 is narrowly formed by inner sides 92 that define the grasping slot 91 formed through the elevator 43. Preferably, the grasping slot 91 is centrally formed through the elevator 43 for receiving a medical device (e.g., catheter or wire guide) and grasping the device during operation of the endoscope.

As depicted in FIG. 2, tip 30 further includes a guide catheter 52 and a wire guide 56 disposed through the guide catheter 52. The tip 30 further includes an elevator 43 configured to receive the guide catheter and/or wire guide for elevating the guide catheter 52 or wire guide 56. As will be described in greater detail below, the elevator 43 is comprised of polymeric material and has a grasping slot formed therethrough for enhanced grasping and reduced scraping purposes.

The elevator 43 is pivotally attached to the tip 30 and is configured to receive the medical instrument (e.g., catheter or wire guide) for elevating the medical instrument. As shown in FIG. 3, the distal tip houses the elevator 43 in channel opening 42. The elevator 43 is used to orient medical instruments such as a catheter. As discussed in greater detail below, this is accomplished by engaging the medical instrument and pivoting away from the distal tip thereby laterally moving the distal end of the medical instrument away from the distal tip. The elevator 43 thus secures the distal end of the medical instrument relative to the endoscope. That is, as the medical instrument is received in slot 91 of the elevator 43, the medical instrument laterally moves relative to the tip 30 when the elevator 43 pivots therefrom.

FIG. 3 illustrates that the endoscope tip 30 includes a cuff 60 as the main body of the tip 30, and a sleeve or cover 62 that covers the perimeter of the cuff 60. As shown, the cover 62 is formed using a nonconductive member such as any suitable polymeric material, e.g., high density polyethylene or polypropylene. In this embodiment, the cover 62 is attached to the cuff 60 by any suitable means, e.g., by adhesive bonding. The cuff 60 is disposed adjacent the working channel 63, which acts as a passageway for the insertion of the medical instrument, e.g., wire guide or catheter. In this embodiment, a channel 67 (FIG. 1c) is formed through the tip 30 such that the tip opening of the treatment instrument is able to be disposed through channel opening 42.

FIG. 3 further illustrates an elevator wire 90 connected to the elevator 43. In this embodiment, the elevator wire 90 is located at the operating portion 25 and extends through a guide tube 92 and a guide pipe 93 connected to the guide tube 92. The elevator wire 90 is in mechanical communication with the control system 14 so that manipulations at the control system 14 result in movement of the elevator wire 90 relative to the endoscope. FIG. 3 depicts (in phantom) movement of the elevator 43 when the elevator wire 90 is actuated at the control system 14, moving the position of the elevator 43 about the elevator turning support 68 as the elevator wire 90 is retracted or pulled.

In this embodiment, the elevator 43 is moved about the elevator turning support 68 by manipulating or actuating the control system 14 to pull or retract the elevator wire 90. As shown in FIG. 5, the result moves the wire guide 56 in the direction of the arrow P and pushes the elevator 43 against the cuff 60. Because the wire guide 56 is formed from a relatively axially stiff material, it tends to remain straight when pushed against the cuff 60, creating a reactive force in the direction of the arrow Fr in FIG. 5. By means of this reactive force, the wire guide 56 is pressed against the slot 91. Moreover, as the elevator 43 and the cuff 60 press against one another, the wire guide is secured.

In another embodiment, FIGS. 4 and 5 illustrate the elevator 43 having a transverse passageways 102 and 103 formed therethrough, each having optional metal sleeves 104 and 105, respectively, disposed thereon. The metal sleeves are configured to provide transverse rigidity to the elevator. The proximal end of the elevator 43 is attached so as to pivot around the elevator turning support 68 provided to the cuff 60.

The elevator 43 is preferably but not necessarily comprised of polymeric material. The polymeric material may include polytetrafluoroethylene (PTFE), polyethylene, polypropylene, perfluoroelastomer, fluoroelastomer, nitrile, neoprene, polyurethane, silicone, styrene-butadiene, rubber, or polyisobutylene, or a mixture thereof. The polymeric material aids the elevator in relatively firmly grasping the medical device while reducing the risk of tearing, scraping, or striping of the medical device.

In one embodiment, the present invention further provides a clip device configured to cooperate with the endoscope 11 and elevator 43 mentioned above. As shown in FIG. 6, the clip device 110 includes a clip 112 with a proximal end 114 having at least three arms 116 extending from the proximal end. Each arm is preferably inwardly bent at its end 118 to better grasp the tissue. While three arms are preferred, it is contemplated that more than three arms may be used. As described in greater detail below, the clip 112 is received in the slot of the elevator for deployment of the clip.

The clip may be made from any suitable resilient material, e.g., stainless steel, nitinol, or plastic. In addition, the arms may have any suitable cross-sectional shape, e.g., a round, square, triangular, pie-shaped, or truncated cone shape.

The proximal end 114 has a first retainer 120 attached to the arms. In one embodiment, the first retainer is permanently attached to the arms. The retainer is provided with a shape that will complement a shape provided on a second retainer so that the first and second retainers will matingly join with each other. For example, the first retainer has a first end 122 and a second end 124 with a notch 126 formed between the first end and the second end. In one embodiment, the first retainer at the first end has a first diameter 123 and at the second end 124, the retainer is in the shape of a half-cylinder having a flat top surface 125. As will be explained in more detail below, this shape advantageously provides secure mating with a complementary second retainer without increasing the diameter beyond that of the first end of the retainer.

The clip device 110 also has an outer sheath 130 (or introducing tube) having an inner diameter that preferably but not necessarily receives an inner sheath 140. The optional inner sheath can be advanced and retracted independently of the outer sheath. The inner sheath has an inner diameter that receives the operating wire 150 having a distal end 152.

The outer sheath is attached at its proximal end to a forward handle portion 180. The inner sheath extends through the forward handle portion 180 and is attached at its proximal end to a middle handle portion 182, which is disposed proximally of the forward handle portion. The operating wire extends through the forward and middle handle portions, and is attached at its proximal end to a rearward handle portion 184, which telescopically extends over the proximal portion of the middle handle portion. As will be explained in more detail below, longitudinal movement of the operating wire and the inner and outer sheaths with respect to each other is controlled by longitudinal manipulation of the forward, middle and rearward handles portions with respect to each other.

The forward handle portion includes a flushing port 186. The flushing port can comprise a standard male or female luer fitting, or any other valve mechanism that permits the injection of fluid therethrough. The flushing port is in fluid communication with the interior volume of the forward handle portion, which in turn is in fluid communication with a cavity or gap 188 that is disposed between the inner and outer sheaths. Accordingly, any fluid injected through the flushing port will necessarily enter the cavity between the inner and outer sheaths, and will subsequently exit the cavity near the distal end 190 of the outer sheath (see FIG. 7). In other words, the fluid injected through the flushing port will exit the clip device near the clip.

Alternatively, the cavity can be disposed inside the inner sheath, or either the inner or the outer sheath can comprise a lumen disposed therein through which fluid can be passed along the length thereof. It should also be understood that the flushing port could be alternatively located on either of the middle or rearward handle portions, or on a portion of the outer sheath distally of any of the handle portions.

A second retainer 160 is attached to the distal end of the operating wire. Preferably, the second retainer is complementary to the first retainer so that the first and second retainers can be matingly joined. Accordingly, the second retainer has a first end 162 and a second end 164 with a notch 166 formed between the first end and the second end. In one embodiment, the second retainer at the first end has a first diameter 163 and at the second end 164, the retainer is in the shape of a half-cylinder having a flat surface 165. In addition, the first diameter of the second retainer is substantially identical to the first diameter of the first retainer.

The first and second retainers are joined with each by locating the flat surface 125 of the first retainer within the notch 166 of the second retainer and by locating the flat surface 165 of the second retainer within the notch 126 of the first retainer. Because the second end of each of the first and second retainers are each about one-half the diameter of the first diameter of their respective retainers, when joined, the first and second retainers form a substantially continuous cylinder shape having substantially the same diameter from the first end of the second retainer to the first end of the first retainer.

It will be understood by one of skill in the art that, although the first and second retainers matingly join with each other, they will not retain a joined position unless they are held together. Accordingly, in a first embodiment, a sliding ring 170 is provided. In this first embodiment, the sliding ring has an inner diameter slightly larger than the first diameter of the first retainer and the second retainer. In other words, the inner diameter of the sliding ring is such that the sliding ring can slide over the retainers yet hold and maintain them in a joined position. As a result, the sliding ring can slide over the first and second retainers to hold them in a mating position. In addition, the sliding ring can slide toward the ends of the arms of the clip causing the arms to move to a closed position lodged within the sliding ring.

In another embodiment, the sliding ring has an inner diameter smaller than the first diameter on the first retainer. As a result, the sliding ring is not removable from the clip. In this embodiment, the sliding ring can be located adjacent the proximal end of the clip so that the arms are in an open position. The sliding ring can then be moved to a position toward the ends of the arms to close them.

The operation of the first embodiment will be described. The outer sheath of the clip device is retracted to expose the operating wire and the second retainer. A clip according to the present invention is provided and the first retainer is matingly joined with the second retainer. The sliding ring is pushed over the first and second retainers so that they are maintained in a joined position.

Next, the outer sheath is pushed toward the distal end of the first retainer and beyond the clip causing the arms of the clip to close. In this state, the outer tube is introduced into a body cavity via a channel of the endoscope 11 that has been previously inserted into the body cavity. While the body cavity is observed via the endoscope, the distal end portion of the outer sheath is guided to a part to be treated. The outer sheath engages the elevator 43 (mentioned above) of the endoscope 11 as the outer sheath carrying the clip is moved past the distal tip of the endoscope. The elevator 43 is positioned proximal the sliding ring.

If the part to be treated is obscured by blood or other bodily fluids, then a fluid such as saline is injected through the flushing port on the forward handle portion. The saline enters the cavity or gap between the inner and outer sheaths, and exits the distal end of the outer sheath. The saline floods the area so as to flush any blood or bodily fluids away from the part to be treated. The injection of saline is continued and/or repeated as necessary during the following steps so as to keep the area free of blood and other bodily fluids.

Alternatively, a vacuum is applied to the flushing port so as to create suction within the cavity or gap between the inner and outer sheaths. This suction can be used to remove blood or other bodily fluids from the area surrounding the part to be treated.

Next, the outer sheath is pulled toward the proximal end (i.e., retracted) to expose the clip and the distal portion of the sliding ring. As the clip and sliding ring are exposed, the operating wire is slidably disposed within the slot of the elevator. The operating wire is retracted to engage the elevator with the sliding ring. Upon engagement, the elevator is pivoted outwardly toward the clip causing the sliding ring to slide toward the arms of the clip causing the arms to close and lodge within the sliding ring. The outer sheath is then retracted and when the distal end of the outer sheath passes the first and second retainers, they detach and release from each other and the clip is left inside the body cavity and lodged within the sliding ring, holding the tissue. After disengaging the retainers, the clip operating device is removed from the channel of the endoscope.

The operation of the second embodiment will be described. The outer sheath of the clip device is retracted to expose the operating wire and the second retainer. The clip according to the present invention is provided and the first retainer is matingly joined with the second retainer. The sliding ring in this embodiment cannot proximally slide and is pushed toward the distal end. The first and second retainers are maintained in a joined position by the outer sheath (or optionally the inner sheath).

Next, the outer sheath is pushed toward the distal end of the first retainer and beyond the clip causing the arms of the clip to close. In this state, the outer tube is introduced into a body cavity via a channel of the endoscope 11 that has been previously inserted into the body cavity. While the body cavity is observed via the endoscope, the distal end portion of the outer sheath is guided to a part to be treated. The outer sheath engages the elevator 43 (mentioned above) of the endoscope 11 as the outer sheath carrying the clip is moved past the distal tip of the endoscope. The elevator is positioned proximal the sliding ring.

Next, the outer sheath is pulled toward the proximal end (i.e., retracted) to expose the clip and the distal portion of the sliding ring. As the clip and sliding ring are exposed, the operating wire is slidably disposed within the slot of the elevator. The operating wire is retracted to engage the elevator with the sliding ring. Upon engagement, the elevator is pivoted outwardly toward the clip causing the sliding ring to slide toward the arms of the clip causing the arms to close within the sliding ring. The outer sheath (and optionally the inner sheath) is then retracted and when the distal end of the inner sheath passes the first and second retainers, they detach and release from each other and the clip is left inside the body cavity and lodged within the sliding ring, holding the tissue. After disengaging the retainers, the clip operating device is removed from the channel of the endoscope.

As noted above, the present invention also contemplates a method of delivering a clip to a target. The method includes providing a clip having a proximal end with at least three arms extending from the proximal end and with a first retainer attached to the proximal end. The first retainer is then matingly joined with a second retainer provided on a distal end of an operating wire that is disposed within an outer sheath. Optionally, an inner sheath, in turn, is slidably disposed over the first and second retainers and within the outer sheath. In other words, the inner sheath may optionally be advanced or retracted independently of the outer sheath. The first retainer and the second retainer are held in a joined position by either a sliding ring or by the outer sheath.

The outer sheath is advanced so that it contacts the clip and forces the arms to a closed position. The outer sheath is then inserted into a channel of an endoscope past the elevator, through the distal end thereof, and directed to the target site.

Once at the target site, the area can be flushed by injecting saline through the flushing port. After the area has been flushed of any blood or other bodily fluids, the outer sheath is retracted to expose the clip and thereby cause the arms to extend to an open position. The clip is then directed to the specific location. As the clip and sliding ring are exposed, the operating wire is slidably disposed within the slot of the elevator. The operating wire is retracted to engage the elevator with the sliding ring. Upon engagement, the elevator is pivoted outwardly toward the clip, so that the sliding ring slides over the arms causing them to close on the target. Thereafter, the outer sheath is retracted and when the outer sheath passes the second end of the second retainer, the first and second retainers release from each other. The outer sheath can then be retracted from the endoscope so that another clip can be loaded.

While the present invention has been described in terms of preferred embodiments, it will be understood, of course, that the invention is not limited thereto since modifications may be made to those skilled in the art, particularly in light of the foregoing teachings.

The invention claimed is:

1. A hemostatic clip delivery system cooperable with an endoscope having an elevator with a slot formed thereon, the system comprising:
   a delivery apparatus comprising an operating wire, an outer sheath and a handle, the operating wire being cooperable with the elevator of the endoscope and slidably disposed within the outer sheath; and
   a hemostatic clip cooperable with the delivery apparatus, the clip comprising a first retainer, a plurality of arms extending distally from the first retainer, and a sliding ring disposed about the plurality of arms, the arms being formed of a resilient material and shaped so that the arms tend to be spaced apart from each other,
   wherein the sliding ring is connected to the operating wire, and
   wherein the outer sheath engages the elevator as the outer sheath is moved in a distal direction, the elevator is positioned next to the sliding ring whereafter the sliding ring is exposed to the slot of the elevator when the outer sheath is pulled in a proximal direction, and the sliding ring engages the elevator when the operating wire is retracted such that the elevator moves the sliding ring toward the arms to close the arms together;
   wherein the outer sheath is separate from the elevator and moveable relative to the elevator.

2. The system of claim 1 wherein the handle includes a flushing port in fluid communication with an interior volume of the apparatus, the flushing port being in fluid communication with a cavity between the outer sheath and operating wire, the flushing port being configured to permit the ingress or egress of fluid from near the clip device.

3. The system of claim 2 wherein the first retainer comprises a first hook and a first notch, and the second retainer comprises a second hook and a second notch, the first hook being configured to engage the second notch, and the second hook being configured to engage the first notch.

4. The system of claim 3 wherein the first retainer and the second retainer each have a generally circular cross-section, the first hook and the second hook each have a semicircular cross-section, and the first notch and the second notch each have a semi-circular cross-section, the cross-sectional area of the first hook and the second hook being greater than that of the first and the second notch.

5. The system of claim 2 wherein the flushing port comprises a standard luer fitting.

6. The system of claim 1 wherein delivery apparatus further comprises a second retainer attached to the operating wire, the second retainer being configured to engage the first retainer of the hemostatic clip so as to temporarily secure the hemostatic clip to the delivery apparatus prior to delivery of the hemostatic clip to a target site.

7. The system of claim 6 wherein the sliding ring is configured to enclose the first retainer and the second retainer prior to delivery of the hemostatic clip to the target site, the sliding ring preventing the first retainer from disengaging from the second retainer, and wherein the sliding ring is movable to a second position to permit the first retainer to disengage from the second retainer when the operating wire is retracted to engage the elevator with the sliding ring.

8. The system of claim 6 wherein the sliding ring comprises a proximal portion and a distal portion, the proximal portion having a first tubular cross-section defining an interior surface that is configured to slidably engage an exterior surface of the first retainer and an exterior surface of the second retainer, and the distal portion having a second tubular cross-section that is configured to slidably engage an outer surface of each of the arms, the second tubular cross-section being smaller than the first tubular cross-section to prevent the sliding ring from being removed from the proximal end of the clip device.

9. The system of claim 1 wherein the distal end of each of the arms comprises an inwardly bent tip portion.

10. The system of claim 1 wherein the clip device comprises three equally spaced arms, each of the arms being curved along a portion between the distal end and the proximal end.

11. An endoscope having a hemostatic clip device for hemostasis, the endoscope comprising:
    an insertion tube extending to a distal tip comprising an elevator with a slot formed therethrough;
    a delivery apparatus disposed through the insertion tube and cooperable with the elevator, the delivery apparatus comprising an operating wire, an outer sheath and a handle, the operating wire being cooperable with the elevator of the distal tip of the endoscope and slidably disposed within the outer sheath; and
    a hemostatic clip cooperable with the delivery apparatus, the clip comprising a first retainer, a plurality of arms extending distally from the first retainer, and a sliding ring disposed about the plurality of arms, the arms being formed of a resilient material and shaped so that the arms tend to be spaced apart from each other,
    wherein the sliding ring is connected to the operating wire, and
    wherein the sliding ring is exposed to the slot of the elevator when the outer sheath is pulled and the sliding ring engages the elevator when the operating wire is retracted such that the elevator pivots toward the hemostatic clip and moves the sliding ring toward the arms to close the arms together.

12. The endoscope of claim 11 wherein delivery apparatus further comprises a second retainer attached to the operating wire, the second retainer being configured to engage the first retainer of the hemostatic clip so as to temporarily secure the hemostatic clip to the delivery apparatus prior to delivery of the hemostatic clip to a target site.

13. The endoscope of claim 12 wherein the sliding ring is configured to enclose the first retainer and the second retainer prior to delivery of the hemostatic clip to the target site, the sliding ring preventing the first retainer from disengaging from the second retainer, and wherein the sliding ring is movable to a second position to permit the first retainer to disengage from the second retainer when the operating wire is retracted to engage the elevator with the sliding ring.

14. The endoscope of claim 12 wherein the first retainer comprises a first hook and a first notch, and the second retainer comprises a second hook and a second notch, the first hook being configured to engage the second notch, and the second hook being configured to engage the first notch.

15. A method of treating a target in a patient, the method comprising:
  providing a hemostatic clip delivery system cooperable with an endoscope having an elevator with a slot formed thereon, the system comprising:
  a delivery apparatus comprising an operating wire, an outer sheath and a handle, the operating wire being cooperable with the elevator of the endoscope and slidably disposed within the outer sheath; and
  a hemostatic clip cooperable with the delivery apparatus, the clip comprising a first retainer, a plurality of arms extending distally from the first retainer, and a sliding ring disposed about the plurality of arms, the arms being formed of a resilient material and shaped so that the arms tend to be spaced apart from each other, wherein the sliding ring is connected to the operating wire;
  introducing the outer sheath through the endoscope to the target;
  moving the outer sheath until the sliding ring is positioned next to the elevator;
  retracting the outer sheath to expose the sliding ring and the clip to the slot of the elevator to extend the arms to an open position;
  slidably disposing the operating wire within the slot of the elevator;
  retracting the operating wire to engage the elevator with the sliding ring; and
  moving the elevator outwardly so that the sliding ring slides over the arms causing the arms to close on the target.

16. The method of claim 15 wherein delivery apparatus further comprises a second retainer attached to the operating wire, the second retainer being configured to engage the first retainer of the hemostatic clip so as to temporarily secure the hemostatic clip to the delivery apparatus prior to delivery of the hemostatic clip to a target site.

17. The method of claim 16 wherein the sliding ring is configured to enclose the first retainer and the second retainer prior to delivery of the hemostatic clip to the target site, the sliding ring preventing the first retainer from disengaging from the second retainer, and wherein the sliding ring is movable to a second position to permit the first retainer to disengage from the second retainer when the operating wire is retracted to engage the elevator with the sliding ring.

18. The method of claim 17 further comprising retracting the outer sheath to release the first and second retainers from each other when the outer sheath exposes the second end of the second retainer.

19. The method of claim 17 wherein the first retainer comprises a first hook and a first notch, and the second retainer comprises a second hook and a second notch, the first hook being configured to engage the second notch, and the second hook being configured to engage the first notch.

20. The method of claim 19 wherein the first retainer and the second retainer each have a generally circular cross-section, the first hook and the second hook each have a semicircular cross-section, and the first notch and the second notch each have a semi-circular cross-section, the cross-sectional area of the first hook and the second hook being greater than that of the first and the second notch.

\* \* \* \* \*